United States Patent
Santhana Naidu et al.

(10) Patent No.: US 10,272,219 B2
(45) Date of Patent: Apr. 30, 2019

(54) CONTROL OF NEONATAL OXYGEN SUPPLY WITH ARTIFACT DETECTION

(71) Applicant: KONINKLIJKE PHILIPS N.V., Eindhoven (NL)

(72) Inventors: Navaneetha Krishnan Santhana Naidu, Bangalore (IN); Rishab Padukone, Chennai (IN); Ganesan Ramachandran, Bangalore (IN); Vishnu Vardhan Makkapati, Ongole (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 693 days.

(21) Appl. No.: 14/758,808

(22) PCT Filed: Jan. 8, 2014

(86) PCT No.: PCT/IB2014/058118
§ 371 (c)(1),
(2) Date: Jul. 1, 2015

(87) PCT Pub. No.: WO2014/118653
PCT Pub. Date: Aug. 7, 2014

(65) Prior Publication Data
US 2015/0335850 A1    Nov. 26, 2015

Related U.S. Application Data

(60) Provisional application No. 61/757,788, filed on Jan. 29, 2013.

(51) Int. Cl.
A61B 5/00 (2006.01)
A61B 5/11 (2006.01)
(Continued)

(52) U.S. Cl.
CPC ........... *A61M 16/1005* (2014.02); *A61B 5/11* (2013.01); *A61B 5/14542* (2013.01);
(Continued)

(58) Field of Classification Search
CPC ... A61B 5/11; A61B 5/14542; A61B 5/14551; A61B 5/4836; A61B 5/721; A61M 16/00;
(Continued)

(56) References Cited

U.S. PATENT DOCUMENTS 4,889,116 A * 12/1989 Taube .................. A61M 16/00
128/204.23
5,025,791 A * 6/1991 Niwa .................. A61B 5/14552
600/324
(Continued)

FOREIGN PATENT DOCUMENTS

DE    102004052753 A1 *  5/2006  ............. A61B 34/70

*Primary Examiner* — Kathryn E Ditmer

(57) ABSTRACT

A system and method to control oxygen supply uses determinations whether physiological sensors and/or a subject interface appliance have been displaced in relation to a subject and/or there has been movement of the subject itself. Artifacts that may reduce the accuracy of measurements of physiological parameters, in particular related to a level of arterial oxygen saturation, may be detected through determinations pertaining to sensor displacement, displacement of the subject interface appliance and/or movement of the subject.

24 Claims, 3 Drawing Sheets

Figure 1:
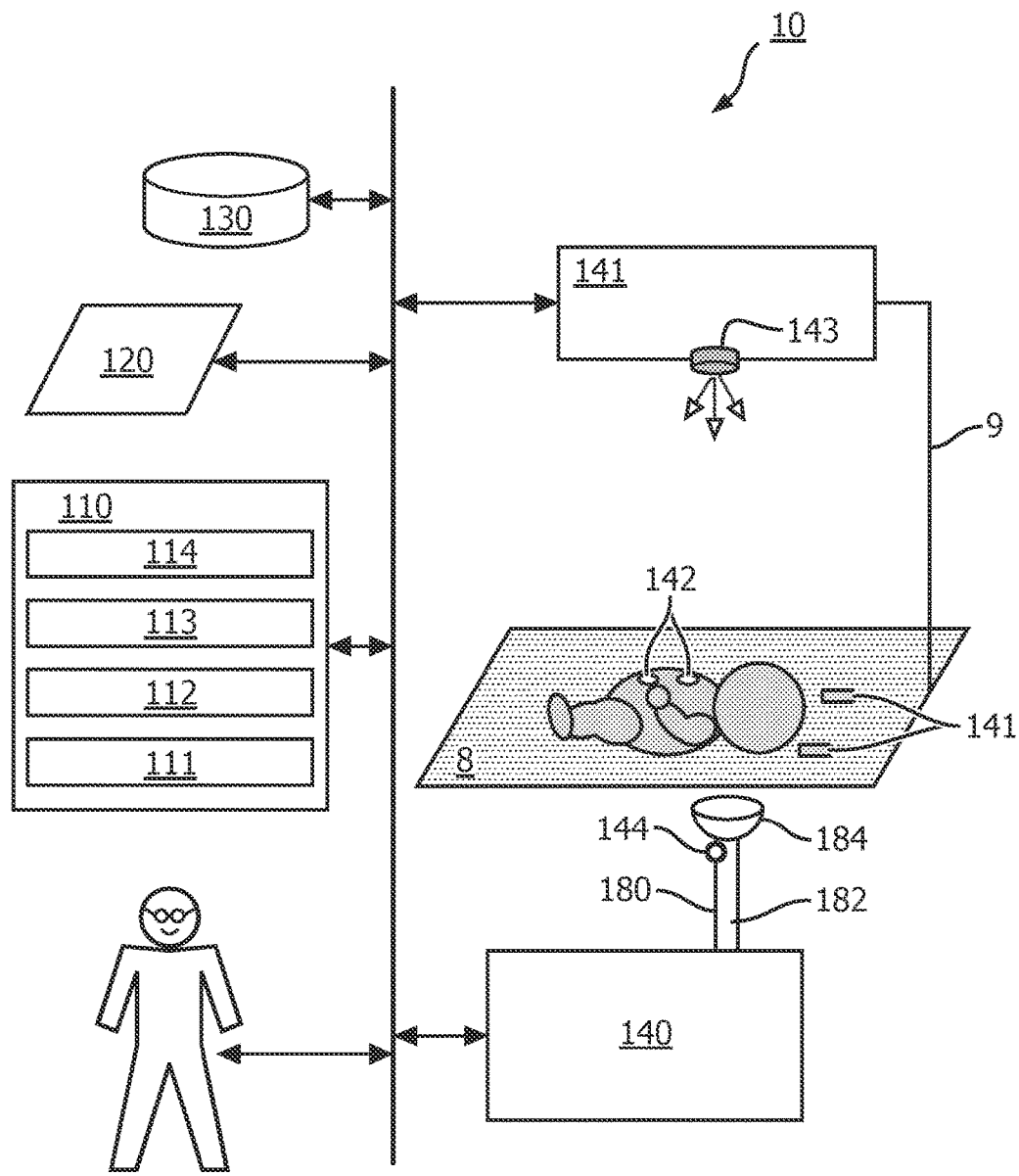

(51) Int. Cl.
*A61B 5/145* (2006.01)
*A61M 16/00* (2006.01)
*A61B 5/1455* (2006.01)
*A61M 16/10* (2006.01)

(52) U.S. Cl.
CPC ............ *A61B 5/4836* (2013.01); *A61B 5/721* (2013.01); *A61M 16/0003* (2014.02); *A61M 16/0051* (2013.01); *A61M 16/0057* (2013.01); *A61M 16/024* (2017.08); *A61B 5/1116* (2013.01); *A61B 5/14551* (2013.01); *A61B 2503/045* (2013.01); *A61M 2016/0027* (2013.01); *A61M 2016/0039* (2013.01); *A61M 2202/0208* (2013.01); *A61M 2205/13* (2013.01); *A61M 2205/17* (2013.01); *A61M 2205/3303* (2013.01); *A61M 2205/3306* (2013.01); *A61M 2205/3334* (2013.01); *A61M 2205/3561* (2013.01); *A61M 2205/3584* (2013.01); *A61M 2205/3592* (2013.01); *A61M 2205/42* (2013.01); *A61M 2205/50* (2013.01); *A61M 2205/505* (2013.01); *A61M 2230/205* (2013.01); *A61M 2230/50* (2013.01); *A61M 2230/62* (2013.01); *A61M 2230/63* (2013.01); *A61M 2240/00* (2013.01)

(58) Field of Classification Search
CPC .......... A61M 16/0003; A61M 16/0051; A61M 16/0057; A61M 16/021; A61M 16/022; A61M 16/024; A61M 16/1005
See application file for complete search history.

(56) References Cited

U.S. PATENT DOCUMENTS

| | | | |
|---|---|---|---|
| 5,365,922 A * | 11/1994 | Raemer | A61B 5/0833 128/202.22 |
| 5,368,026 A | 11/1994 | Swedlow et al. | |
| 5,505,199 A | 4/1996 | Kim | |
| 6,371,114 B1 * | 4/2002 | Schmidt | A61M 16/026 128/204.23 |
| 7,123,758 B2 | 10/2006 | Jeung et al. | |
| 7,378,975 B1 * | 5/2008 | Smith | A61B 5/1126 340/573.1 |
| 7,814,906 B2 | 10/2010 | Moretti | |
| 7,890,153 B2 * | 2/2011 | Hoarau | A61B 5/062 600/323 |
| 7,942,824 B1 * | 5/2011 | Kayyali | A61B 5/021 128/204.23 |
| 2006/0270920 A1 * | 11/2006 | Al-Ali | A61B 5/14551 600/323 |
| 2008/0021731 A1 * | 1/2008 | Rodgers | A61B 5/1113 705/2 |
| 2008/0114211 A1 * | 5/2008 | Karst | A61B 5/0402 600/300 |
| 2010/0094107 A1 * | 4/2010 | Lamego | A61B 5/061 600/322 |
| 2010/0208063 A1 * | 8/2010 | Lee | G06K 9/00771 348/143 |
| 2010/0224191 A1 * | 9/2010 | Dixon | A61B 5/145 128/204.23 |

* cited by examiner

CONTROL OF NEONATAL OXYGEN SUPPLY WITH ARTIFACT DETECTION

CROSS-REFERENCE TO PRIOR APPLICATIONS

This application is the U.S. National Phase application under 35 U.S.C. § 371 of International Application No. PCTS/IB2014/058118, filed on Jan. 8, 2014, which claims the benefit of U.S. Provisional Patent Application No. 61/757,788, filed on Jan. 29, 2013. These applications are hereby incorporated by reference herein.

The present disclosure pertains to systems and methods for controlling oxygen supply to a subject, and, in particular, to systems and methods that detect whether sensor-based measurements of arterial oxygen saturation of an infant suffer as a result of displacement of one or more sensors, a subject interface appliance, and/or movement of the subject.

Infants, e.g. neonates, sometimes need respiratory therapy, in particular supply of breathable gas having oxygen levels above those of ambient air. Infants may be monitored such that their level of arterial oxygen saturation (SpO2) is controlled within a predetermined range. By supplying breathable gas with a particular fraction of inhaled oxygen, the respiratory therapy may be used to control $SpO_2$ levels. Measurements of arterial oxygen saturation may be inaccurate for a variety of reasons. This inaccuracy may, in turn, affect the performance and/or effectiveness of the task of controlling respiratory therapy to maintain $SpO_2$ levels.

Accordingly, it is an object of one or more embodiments of the present invention to provide a system for controlling oxygen supply for a subject having an airway. The system comprises a pressure generator, a plurality of physiological sensors, one or more position sensors, one or more processors, and various executable computer program modules. The pressure generator is configured to generate a pressurized flow of breathable gas for delivery to the airway of the subject. The pressurized flow of breathable gas may be delivered through a subject interface appliance. The plurality of physiological sensors is configured to generate output signals conveying physiological information related to one or more physiological parameters. The one or more position sensors are configured to generate output signals conveying position information related to one or more of the physiological sensors with respect to the subject, the subject interface appliance, and/or to other ones of the physiological sensors. The one or more processors are configured to execute computer program modules. The computer program modules include an artifact module, a parameter determination module, and an oxygen control module. The artifact module is configured to detect displacement of the physiological sensors, the subject interface appliance, and/or movement of the subject that could result in artifacts in determinations of the level of arterial oxygen saturation by the parameter determination module. The artifact module is configured to detect such displacement based on the output signals generated by the one or more position sensors. The parameter determination module is configured to determine a level of arterial oxygen saturation of the subject based on the output signals generated by the physiological sensors. The oxygen control module is configured to adjust the pressurized flow of breathable gas and/or a fraction of inspired oxygen therein based on the determined level of arterial oxygen saturation and detections of displacement by the artifact module.

It is yet another aspect of one or more embodiments of the present invention to provide a method of controlling oxygen supply for a subject, the subject having an airway. The method is implemented using a system that includes a pressure generator, a plurality of physiological sensors, and one or more position sensors. The method comprises generating a pressurized flow of breathable gas for delivery to the airway of the subject through a subject interface appliance; generating output signals conveying physiological information related to one or more physiological parameters of the subject; generating output signals conveying position information related to one or more of the physiological sensors with respect to the subject, the subject interface appliance, and/or to other ones of the physiological sensors; determining a level of arterial oxygen saturation of the subject based on the output signals generated by the physiological sensors; detecting displacement of one or more of the physiological sensors, the subject appliance interface, and/or detecting movement of the subject that could result in artifacts in determinations of the level of arterial oxygen supply, wherein the detections are based on the output signals generated by the one or more position sensors; and adjusting the pressurized flow of breathable gas and/or a fraction of inspired oxygen therein based on the determined level of arterial oxygen saturation and the detections of displacement.

It is yet another aspect of one or more embodiments to provide a system configured to control oxygen supply for a subject having an airway. The system comprises means for generating a pressurized flow of breathable gas for delivery to the airway of the subject; first means for generating output signals conveying physiological information related to one or more physiological parameters of the subject; second means for generating output signals conveying position information related to one or more of the first means with respect to the subject and/or the first means; first means for determining a level of arterial oxygen saturation of the subject based on the output signals generated by the first means for generating; second means for detecting whether the first means for generating and/or the subject has been displaced in a way that could result in artifacts in determinations by the first means, wherein operation of the second means for detecting is based on the output signals generated by the second means for generating; and means for adjusting the pressurized flow of breathable gas and/or a fraction of inspired oxygen therein based on determinations by the first means for determining and detections by the second means for detecting.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

Figure 2:
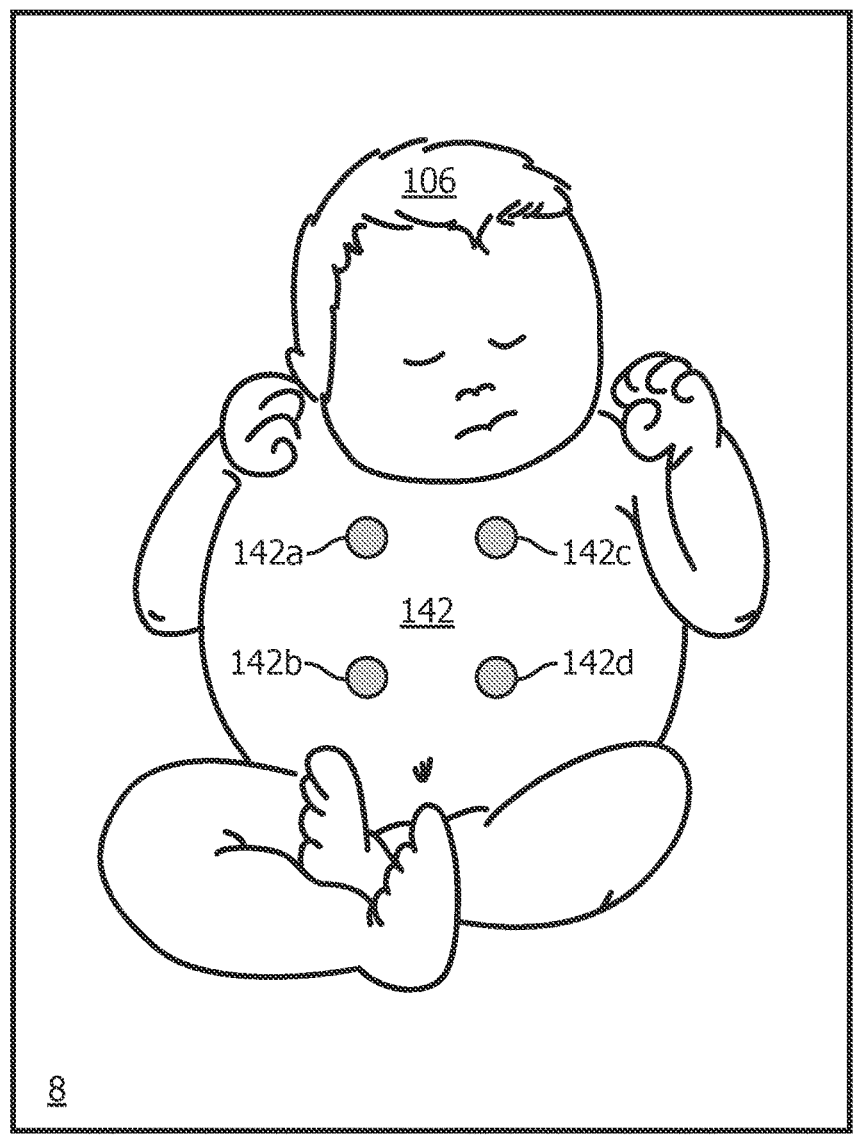
Figure 3:
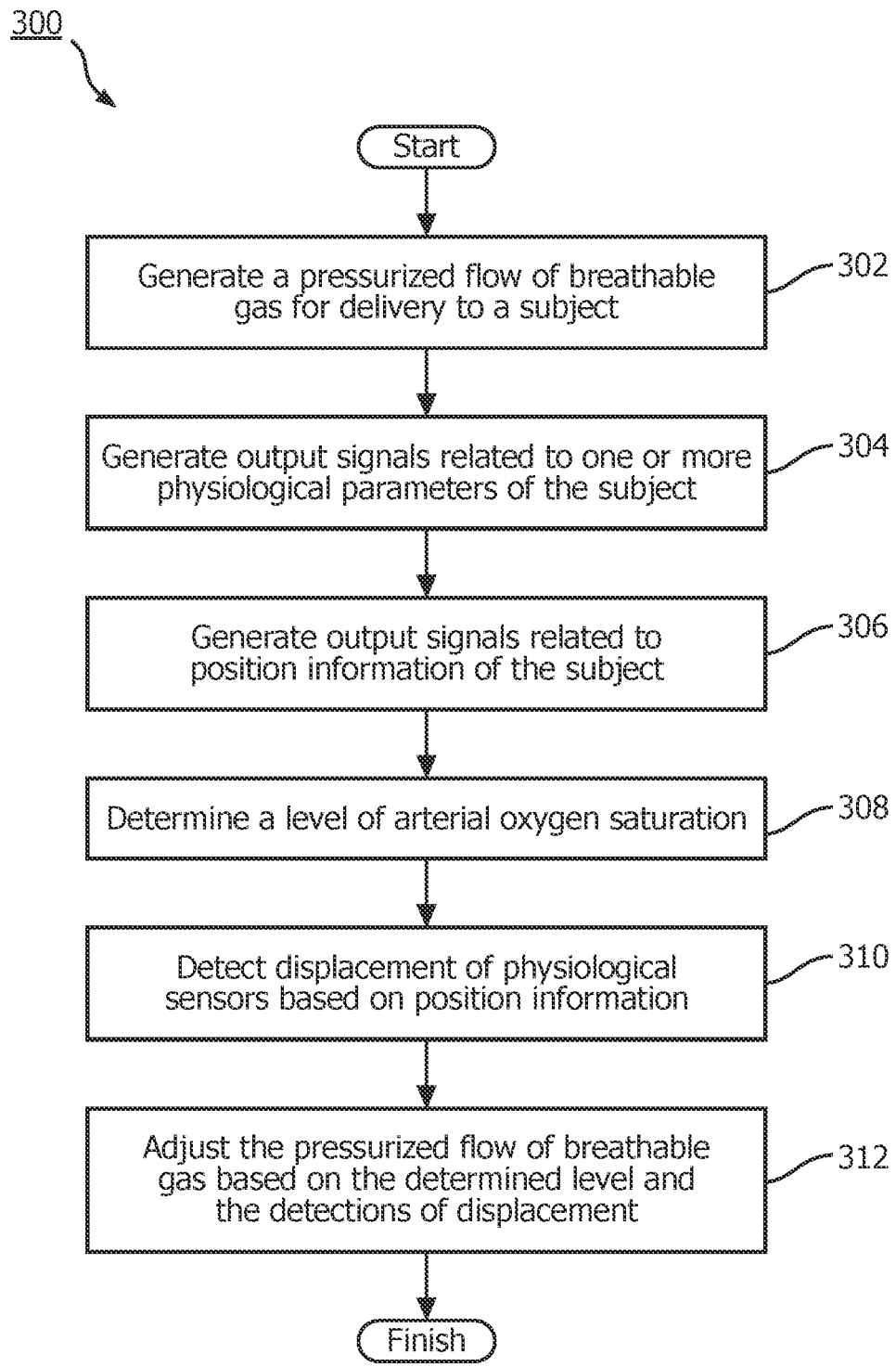

FIG. 1 schematically illustrates a system for controlling oxygen supply in accordance with one or more embodiments;

FIG. 2 illustrates a view of a plurality of physiological sensors on a subject in accordance with one or more embodiments; and FIG. 3 illustrates a method for controlling oxygen supply in accordance with one or more embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a system 10 in accordance with one or more embodiments. The view in FIG. 1 combines aspects from different perspectives and is not intended to be limiting in any way. System 10 may include one or more of an subject-supporting body 8, support structure 9, a plurality of physiological sensors 142, one or more position sensors 141, one or more flow, oxygen, and/or pressure sensors 144, one or more processors 110, a position module 111, an artifact module 112, a parameter determination module 113, an oxygen control module 114, a user interface 120, electronic memory 130, a pressure generator 140, a delivery circuit 180, a subject interface appliance 184, and/or other components.

Subject-supporting body 8 may be configured to support and physically engage subject 106. Subject 106 may be an infant, neonate, and/or other subject or patient. In some embodiments, one or more sensors may be integrated, embedded, combined, and/or connected with subject-supporting body 8. Support structure 9 may be configured to support and/or carry one or more position sensors 141, e.g. fixed in place, and may interchangeably referred to as a stand. In some embodiments, system 10 may not include subject-supporting body 8 and/or support structure 9. Some embodiments may include fewer components than depicted in FIG. 1.

During various types of therapy, including but not limited to respiratory therapy, one or more physiological parameters of subject 106 may be measured and/or monitored. The physiological parameters may include, but are not limited to, (arterial) oxygen saturation, heart rate, respiration rate, etc. One or more physiological parameters may be used, e.g. in a feedback manner, to control one or more parameters of a pressurized flow of breathable gas being delivered to subject 106. The one or more controlled parameters may include, but are not limited to, the supply of oxygen to subject 106 through the pressurized flow of (oxygen-enriched) breathable gas, and/or the control of the fraction of oxygen therein.

Effective and/or appropriate levels of (respiratory) therapy and/or oxygen-enriched breathable gas may be based on the subject's age, size, weight, and/or other physiological, environmental, ambient, and/or subject-specific parameters. The subject-specific parameters may be adjusted according to clinical guidelines.

Pressure generator 140 of system 10 in FIG. 1 may be integrated, embedded, combined, and/or connected with a ventilator system and/or a (non-invasive) positive airway pressure device (PAP/CPAP/BiPAP®/etc.). Pressure generator 140 may be configured to provide a pressurized flow of breathable gas for delivery to the airway of subject 106, e.g. via delivery circuit 180. Breathable gas may be provided to subjects not capable of (or in need of help with) properly breathing due to one or more reasons, including but not limited to respiratory muscle weakness, neuromuscular disease, atrophy, dysfunction, and/or other reasons. Pressure generator 140 may be configured as a flow generator. The terms pressure generator and flow generator may be used interchangeably herein. Subject 106 may or may not initiate one or more phases of respiration. For example, one or more embodiments may include active ventilation during inspiration and passive ventilation during exhalation. By supplying breathable gas with a particular fraction of inhaled oxygen, pressure generator 140 may be used to control $SpO_2$ levels.

During inspiration, the pressure of the pressurized flow of breathable gas may be adjusted to one or more inspiratory pressure levels to induce, support, and/or control inhalation by subject 106. Alternatively, and/or additionally, during expiration, the pressure of the pressurized flow of breathable gas may be adjusted to one or more expiratory pressure levels to induce, support, and/or control exhalation by subject 106. Pressure generator 140 is configured to adjust one or more of a pressure level, flow rate, oxygen fraction, humidity, velocity, acceleration, and/or other parameters of the pressurized flow of breathable gas.

A pressurized flow of breathable gas is delivered from pressure generator 140 to the airway of subject 106 via delivery circuit 180. The pressurized flow may have a particular fraction of oxygen. Delivery circuit 180 may be configured to selectively control the direction and/or other parameters of the delivery of breathable gas to and/or from the airway of subject 106. Delivery circuit 180 may interchangeably be referred to as subject interface 180. Delivery circuit 180 may include a conduit 182, a subject interface appliance 184, and/or other constituent components. Conduit 182 includes a flexible length of hose, or other conduit, either in a single-limb or multi-limb configuration that places subject interface appliance 184 in fluid communication with pressure generator 140. Conduit 182 forms a flow path through which the pressurized flow of breathable gas is communicated between subject interface appliance 184 and pressure generator 140.

Subject interface appliance 184 of system 10 in FIG. 1 is configured to deliver the pressurized flow of breathable gas to the airway of subject 106. Subject interface appliance 184 may interchangeably be referred to as a gas delivery device. As such, subject interface appliance 184 may include any appliance suitable for this function. In some embodiments, the breathable gas is delivered non-invasively. In some embodiments, pressure generator 140 is a dedicated ventilation device and subject interface appliance 184 is configured to be removably coupled with another interface appliance being used to deliver respiratory therapy to subject 106. For example, subject interface appliance 184 may be configured to engage with and/or be inserted into an endotracheal tube, a tracheotomy portal, and/or other interface appliances. In one embodiment, subject interface appliance 184 is configured to engage the airway of subject 106 without an intervening appliance. In this embodiment, subject interface appliance 184 may include one or more of an endotracheal tube, a nasal cannula, a tracheotomy tube, a nasal mask, one or more nasal prongs, a nasal/oral mask, a full-face mask, a total facemask, a head box, and/or other interface appliances that communicate a flow of gas with an airway of a subject. The present disclosure is not limited to these examples, and contemplates delivery of the pressurized flow of breathable gas to subject 106 using any subject interface.

The sensors of system 10 may include a plurality of physiological sensors 142, one or more position sensors 141, one or more flow, oxygen, and/or pressure sensors 144, and/or other sensors.

Individual ones of the plurality of physiological sensors 142 of system 10 in FIG. 1 may be configured to generate output signals conveying physiological information related to one or more physiological parameters of subject 106. In some embodiments, the conveyed information may be related to parameters associated with the state and/or condition of subject 106, the breathing of subject 106, the gas breathed by subject 106, the heart rate of subject 106, the respiratory rate of subject 106, vital signs of subject 106, including one or more temperatures, oxygen saturation of arterial blood ($SpO_2$), whether peripheral or central, physiological, environmental, and/or subject-specific (medical) parameters, and/or other parameters. For example, the plurality of physiological sensors 142 may include one or more pulse oximeters. The measured level of (arterial) oxygen saturation may be used, e.g. in a feedback manner, to control one or more parameters of the pressurized flow of oxygen-enriched breathable gas being delivered to subject 106, in particular the fraction of oxygen in the oxygen-enriched breathable gas.

Physiological sensors 142 may produce inaccurate measurements for a variety of reasons. For example, an individual physiological sensor 142 may be displaced by movements and/or actions of subject 106. In case of an infant, a particular sensor may for example be grabbed by the infant, which may reduce the reliability of the measurements using that particular sensor. Sensors may be displaced during routine care of subjects, including but not limited to feeding and changing diapers for infants.

Individual ones of the one or more position sensors 141 of system 10 in FIG. 1 may be configured to generate output signals conveying information, e.g. position information. The position information may be related to one or more of the location, position, posture, size, weight, and/or status of subject 106, the absolute or relative position of one or more physiological sensors 142, and/or other information. The position information may include a three-dimensional location, a two-dimensional location, the presence, the orientation, relative spatial information, and/or other information pertaining to subject 106 and/or one or more physiological sensors 142. For example, pertaining to an infant, the position information may include a location of a specific (body) part (e.g., eyes, arms, legs, a face, a head, a forehead, and/or other anatomical parts of subject 106), a location of subject 106 as a whole, the posture of subject 106, whether subject 106 is in a supine position, the orientation of subject 106 or one or more anatomical parts of subject 106, relative spatial information pertaining to subject 106 or one or more anatomical parts of subject 106, and/or other infant-specific information. One or more position sensors 141 may be configured to generate output signals conveying information that may be used to determine whether one or more physiological sensors 142 have been displaced. System 10 may use any of the generated output signals to monitor subject 106.

In some embodiments, the one or more position sensors 141 may include an image capture device 143 configured to capture image data. The captured image data may include position information related to subject 106 and/or one or more physiological sensors 142, and/or the relative position or distance therebetween. Image capture device 143 may include one or more of a still-image camera, a video-camera, and/or other imaging sensor suitable for capturing image data. Alternatively, and/or simultaneously, the one or more position sensors 141 may include one or more of a temperature sensor, one or more pressure/weight sensors, one or more light sensors, one or more electromagnetic (EM) sensors, one or more infra-red (IR) sensors, and/or other sensors and combinations thereof. For example, position information may be conveyed by output signals of a set or array of infra-red sensors, e.g. arranged around the periphery of subject-supporting body 8.

The one or more flow, oxygen, and/or pressure sensors 144 may be configured to generate output signals conveying information related to the pressurized flow of breathable gas and/or a fraction of oxygen therein at or near a point of delivery to subject 106. The conveyed information may include or pertain to one or more gas parameter. These gas parameters may include one or more of flow, (airway) pressure, barometric pressure, temperature, humidity, velocity, acceleration, composition, and/or other gas parameters. For example, the composition of the pressurized flow of breathable gas may include a particular fraction of oxygen. One or more flow, oxygen, and/or pressure sensors 144 may be in fluid communication with conduit 182, subject interface appliance 184, and/or other components of system 10. For example, a gas parameter may be related to a mechanical unit of measurement of a component of pressure generator 140 (or of a device that pressure generator 140 is integrated, combined, or connected with) such as valve drive current, rotor speed, motor speed, blower speed, fan speed, or a related measurement that may serve as a proxy for any of the previously listed parameters through a previously known and/or calibrated mathematical relationship. Resulting signals or information from one or more flow, oxygen, and/or pressure sensors 144 may be transmitted to processor 110, user interface 120, electronic storage 130, and/or other components of system 10. This transmission may be wired and/or wireless.

The illustration of the plurality of physiological sensors 142 as including two members in FIG. 1 is not intended to be limiting. The illustration of one or more position sensors 141 as including a specific number of members in FIG. 1 is not intended to be limiting. The illustration of one flow, oxygen, and/or pressure sensor 144 in FIG. 1 is not intended to be limiting. System 10 may include any number of sensors. The illustration of a particular symbol or icon for any sensor in FIG. 1 is exemplary and not intended to be limiting in any way. Resulting signals or information from any sensor may be transmitted to processor 110, user interface 120, electronic storage 130, and/or other components of system 10. This transmission can be wired and/or wireless.

User interface 120 of system 10 in FIG. 2 may be configured to provide an interface between system 10 and a user (e.g., user 108, a caregiver, a healthcare provider, a therapy decision-maker, etc.) through which the user can provide information to and/or receive information from system 10. This enables data, results, and/or instructions and any other communicable items, collectively referred to as "information," to be communicated between the user and system 10. An example of information that may be conveyed to user 108 is a report detailing the changes in monitored vital signs throughout a period during which subject 106 is present near system 10 or undergoing therapy. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 by user interface 120 in the form of auditory signals, visual signals, tactile signals, and/or other sensory signals, or any combination thereof.

By way of non-limiting example, user interface 120 may include a radiation source capable of emitting light. The radiation source may include, for example, one or more of at least one LED, at least one light bulb, a display screen, and/or other sources. User interface 120 may control the radiation source to emit light in a manner that conveys information to user 108.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 10 from removable storage (e.g., a smart card, a flash drive, a removable disk, etc.) that enables the user(s) to customize the implementation of system 10. Other exemplary input devices and techniques adapted for use with system 10 as user interface 120 include, but are not limited to, an RS-232 port, RF link, an IR link, modem (telephone, cable, Ethernet, internet or other). In short, any technique for communicating information with system 10 is contemplated as user interface 120.

Electronic storage 130 of system 10 in FIG. 1 comprises electronic storage media that electronically stores information. The electronic storage media of electronic storage 130 may include one or both of system storage that is provided integrally (i.e., substantially non-removable) with system 10 and/or removable storage that is removably connectable to system 10 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 10 to function properly. For example, electronic storage 130 may record or store information related to the oxygen saturation as measured over a period of time, and/or other information. Electronic storage 130 may be a separate component within system 10, or electronic storage 130 may be provided integrally with one or more other components of system 10 (e.g., processor 110).

Processor 110 of system 10 in FIG. 1 is configured to provide information processing capabilities in system 10. As such, processor 110 includes one or more of a digital processor, an analog processor, a digital circuit designed to process information, an analog circuit designed to process information, and/or other mechanisms for electronically processing information. Although processor 110 is shown in FIG. 1 as a single entity, this is for illustrative purposes only. In some implementations, processor 110 includes a plurality of processing units.

As is shown in FIG. 1, processor 110 is configured to execute one or more computer program modules. The one or more computer program modules include one or more of a position module 111, an artifact module 112, a parameter determination module 113, an oxygen control module 114, and/or other modules. Processor 110 may be configured to execute modules 111-114 by software; hardware; firmware; some combination of software, hardware, and/or firmware; and/or other mechanisms for configuring processing capabilities on processor 110.

It should be appreciated that although modules 111-114 are illustrated in FIG. 1 as being co-located within a single processing unit, in implementations in which processor 110 includes multiple processing units, one or more of modules 111-114 may be located remotely from the other modules. The description of the functionality provided by the different modules 111 and/or 112 described below is for illustrative purposes, and is not intended to be limiting, as any of modules 111 and/or 112 may provide more or less functionality than is described. For example, one or more of modules 111-114 may be eliminated, and some or all of its functionality may be provided by other ones of modules 111-114. Note that processor 110 may be configured to execute one or more additional modules that may perform some or all of the functionality attributed below to one of modules 111 and/or 112.

Parameter determination module 113 of system 10 may be configured to determine one or more status parameters, medical parameters, and/or other parameters from output signals generated by one or more sensors. Determined parameters may be related to physiological, environmental, and/or subject-specific parameters. One or more physiological parameters may be related to monitored vital signs of subject 106, and/or other medical parameters of subject 106. Other parameters may be related to the environment near system 10, such as, e.g., air temperature and/or other ambient parameters.

In some embodiments, parameter determination module 113 may be configured to determine a level of (arterial) oxygen saturation of subject 106. Determinations by parameter determination module may be based on output signals generated by individual ones of the plurality of physiological sensors 142, individual ones of the one or more position sensors 141, individual ones of the one or more flow, oxygen, and/or pressure sensors 144, and/or other sensors.

Position module 111 of system 10 in FIG. 1 may be configured to determine one or more positions of subject 106 and/or individual ones of the plurality of physiological parameters 142. Determinations by position module 111 may be based on output signals generated by individual ones of the one or more position sensors 141. Determinations by position module 111 may be used in other components of system 10. In some embodiments, determination by position module 111 may be based on information from image capture device 143, e.g. through stereoscopy. Image capture device 143 may be arranged to capture image data conveying visual information related to the position of subject 106, the plurality of physiological sensors on subject 106, and/or the relative position therebetween. For example, a camera may capture images of a top-view of subject 106, e.g. by virtue of being positioned above subject 106 at a suitable angle and distance. A lens (or other constituent component of a camera along the path from visual information to captured image data) may insert, add, and/or superimpose a grid in/to/on the captured image. Alternatively, and/or simultaneously, a component may be used to add grid information to the captured image data. For example, a grid may be depicted on a top-surface of subject-supporting body 8. One or more determinations by position module 111 may be based on grid information and/or the captured image data.

By way of illustration, FIG. 2 illustrates a top-view of a plurality of physiological sensors 142 on subject 106. As depicted, the plurality includes physiological sensors 142a, 142b, 142c, and 142d. Locations of the physiological sensors may be monitored and/or tracked to determine whether an individual physiological sensor has been displaced. Displacement may be determined relative to subject 106, relative to one or more other physiological sensors, relative to another point of reference, and/or any combination thereof.

Artifact module 112 of system 10 in FIG. 1 may be configured to detect and/or determine whether displacements and/or artifacts have occurred. Artifacts are events that may reduce the accuracy of measurements, e.g. measurements using individual ones of the plurality of physiological sensors 142. The accuracy of measurements may, e.g., be reduced by sensor displacement, movement of subject 106, and/or other events. In some embodiments, artifact module 112 may be configured to detect whether individual ones of the plurality of physiological sensors 142 have been displaced.

Detections by artifact module 112 may be based on output signals generated by one or more position sensors 141, including but not limited to image capture device 143. For example, such detections may be based on one or more positions as determined by position module 111 and/or position information as included in captured image data by image capture device 143. In some embodiments, artifact module 112 may be configured to detect whether individual ones of the plurality of physiological sensors 142 have been displaced by tracking locations of individual physiological sensors 142 over a period of time and/or over a plurality of images. For example, tracking may be relative to other sensors. The period of time may depend on the rate of generating output signals (by one or more position sensors 141 and/or image capture device 143. The period of time may be about 1 ms, about 10 ms, about 0.1 second, about 1 second, about 10 seconds, about 30 seconds, about 1 minute, and/or another suitable period that is sufficiently granular for controlling oxygen saturation for a particular subject.

For example, in embodiments using a video camera, artifact module 112 may be configured to track the locations of individual physiological sensors 142 over multiple frames of video data by detecting individual sensors in individual frames of video data, determining the configuration and/or distances between multiple sensors, and comparing those determinations with historical averages. Other approaches to detect displacement are considered within the scope of this disclosure. For example, the steps may include segmentation, labeling of sensors within frames of video data, association of the sensors to each other, parts of subject 106, and/or other visible reference objects, and tracking of sensor positions between multiple frames of video data.

In some embodiments, artifact module 112 may be configured to detect and/or determine whether one or more blockages of flow have occurred during the delivery of the pressurized flow of breathable gas. For example, a nasal blockage may reduce or prevent the flow rate of a delivered flow of breathable gas to subject 106. Such a blockage may be detected by monitoring output signals generated by one or more flow, oxygen, and/or pressure sensors 144. Artifact module 112 may be configured to generate an alarm and/or notification, e.g. for a caregiver, if the level or type of detected artifact breaches a threshold level of severity that indicates rapid intervention is warranted and/or desirable.

Oxygen control module 114 may be configured to control and/or adjust one or more of the pressurized flow of breathable gas and/or a fraction of oxygen in the pressurized flow of breathable gas. Adjustments may pertain to one or more parameters of the pressurized flow of breathable gas. In some embodiments, the parameters include a fraction of oxygen in the pressurized flow. For example, oxygen control module 114 may be configured to respond to a determination that a measured fraction of oxygen in the delivered flow of breathable gas has fallen outside of a target range. By adjusting one or more parameters accordingly, e.g. in a feedback manner, the pressurized flow of breathable gas may maintain a target level for the fraction of oxygen delivered. Alternatively, and/or simultaneously, adjustments may correspond to a determination that a measured level of oxygen saturation of subject 106 has fallen outside of a target range. Target levels or ranges may depend on one or more of age, weight, size, and/or other subject-specific characteristics or properties. For example, a target range of oxygen saturation for an infant may be between about 87% and about 92%. Both excess and deficient oxygen supply may be undesirable. By adjusting one or more parameters of the pressurized flow accordingly, e.g. in a feedback manner, the pressurized flow of breathable gas may be controlled such that a target level or range of oxygen saturation is maintained (and/or reached). Feedback control may include closed-loop control.

Adjustments and/or control by oxygen control module 114 may be based on detections by artifact module 112. For example, responsive to a detection by artifact module 112 that a particular physiological sensor 142 has been displaced in relation to subject 106 and/or other sensors, output signals generated by that particular physiological sensor may be known to have a reduced accuracy. By taking such a displacement and/or the reduced accuracy into account when controlling one or more parameters of the pressurized flow of breathable gas, oxygen control module 114 may prevent unnecessary and/or possibly detrimental adjustments, including but not limited to over-oxygenating subject 106.

FIG. 3 illustrates a method 300 for controlling oxygen supply for subject 106. The operations of method 300 presented below are intended to be illustrative. In some embodiments, method 300 may be accomplished with one or more additional operations not described, and/or without one or more of the operations discussed. Additionally, the order in which the operations of method 300 are illustrated in FIG. 3 and described below is not intended to be limiting.

In some embodiments, method 300 may be implemented in one or more processing devices (e.g., a digital processor, an analog processor, a digital circuit designed to process information, an analog circuit designed to process information, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, a pressurized flow of breathable gas is generated for delivery to the airway of the subject. In some embodiments, operation 302 is performed by a pressure generator the same as or similar to pressure generator 140 (shown in FIG. 1 and described herein).

At an operation 304, output signals are generated that convey physiological information related to one or more physiological parameters of the subject. In some embodiments, operation 304 is performed by a plurality of physiologic sensors the same as or similar to plurality of physiological sensors 142 (shown in FIG. 1 and described herein).

At an operation 306, output signals are generated that convey position information related to one or more of the subject, the subject interface appliance, and/or individual ones of the plurality of physiological sensors. In some embodiments, operation 306 is performed by one or more position sensors the same as or similar to position sensors 141 (shown in FIG. 1 and described herein).

At an operation 308, a level of arterial oxygen saturation of the subject is determined based on the output signals generated by one or more of the plurality of physiological sensors. In some embodiments, operation 308 is performed by a parameter determination module the same as or similar to parameter determination module 113 (shown in FIG. 1 and described herein).

At an operation 310, displacement of physiological sensors is detected based on the output signals generated by the one or more position sensors. In some embodiments, operation 310 is performed by an artifact module the same as or similar to artifact module 112 (shown in FIG. 1 and described herein).

At an operation 312, the pressurized flow of breathable gas is adjusted based on the determined level of arterial oxygen saturation and the detections of displacement. In some embodiments, operation 312 is performed by an oxygen control module the same as or similar to oxygen control module 114 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system for controlling oxygen supply for a subject having an airway, the system comprising:
   a pressure generator configured to generate a pressurized flow of breathable gas for delivery to the airway of the subject, wherein the pressurized flow of breathable gas is delivered through a subject interface appliance;
   a plurality of physiological sensors configured to generate output signals conveying physiological information related to one or more physiological parameters of the subject;
   one or more position sensors configured to generate output signals conveying position information related to one or more of the physiological sensors with respect to the subject, the subject interface appliance, and/or to other ones of the physiological sensors, wherein the one or more position sensors are not coupled to the subject and output video data;
   one or more processors configured to execute computer program modules, the computer program modules comprising:
   a parameter determination module configured to determine a level of arterial oxygen saturation of the subject based on the output signals generated by the physiological sensors;
   an artifact module configured to detect displacement of the physiological sensors that could result in artifacts in determinations of the level of arterial oxygen saturation by the parameter determination module, wherein the artifact module is configured to detect such displacement based on the output signals generated by the one or more position sensors, wherein detecting displacement comprises detecting individual sensors of the plurality of physiological sensors in the video data, determining distances between the plurality of physiological sensors, and comparing those determinations with historical averages for the distances between the plurality of physiological sensors; and
   an oxygen control module configured to adjust one or more of the pressurized flow of breathable gas and/or a fraction of oxygen in the pressurized flow of breathable gas based on the determined level of arterial oxygen saturation and detections of displacement by the artifact module.

2. The system of claim 1, further comprising a position module configured to determine one or more positions of individual ones of the physiological sensors based on the output signals generated by the one or more position sensors.

3. The system of claim 1, wherein the one or more position sensors include an image capture device configured to capture image data such that, after the image capture device and the subject are arranged in suitable proximity, the captured image data include position information, wherein detections by the artifact module are further based on the captured image data.

4. The system of claim 3, wherein the image capture device is configured to capture a top-view of the subject and insert, add, and/or superimpose a grid on a captured image to determine, relative to the grid, the position information related to one or more of the physiological sensors, and/or the subject interface appliance.

5. The system of claim 1, further comprising a flow and/or pressure sensor configured to generate output signals conveying information related to the delivery of the pressurized flow of breathable gas to the subject, wherein the artifact module is further configured to detect whether delivery of the pressurized flow of breathable gas is obstructed based on the output signals generated by the flow and/or pressure sensor.

6. The system of claim 1, wherein the artifact module is configured to detect whether individual ones of the physiological sensors have been displaced by tracking locations of individual ones of the physiological sensors over time.

7. The system of claim 1, wherein the one or more position sensors is located on a structure spaced apart from the subject such that the one or more positions is not carried by the subject.

8. The system of claim 7, wherein the one or more position sensors includes a first position sensor attached to a subject-supporting body configured to support the subject, and a second position sensor attached to a stand configured to carry the second position sensor.

9. The system of claim 1, wherein the artifact module is further configured to:
   detect displacement by segmenting the video data, and labeling the plurality of physiological sensors within frames of the video data;
   associate the plurality of physiological sensors to each other, parts of the subject, and/or other visible reference objects; and
   track positions of the plurality of physiological sensors relative to each other, the parts of the subject, and/or the other visible reference objects between multiple frames of video data.

10. The system of claim 1, wherein the oxygen control module is further configured to adjust the one or more of the pressurized flow of breathable gas and/or the fraction of oxygen in the pressurized flow of breathable gas in response to a detection by the artifact module that a particular physiological sensor has been displaced in relation to other sensors of the plurality of physiological sensors.

11. The system of claim 1, wherein the oxygen control module is further configured to adjust the one or more of the pressurized flow of breathable gas and/or the fraction of oxygen in the pressurized flow of breathable gas in a feedback manner such that a target level of oxygen saturation is maintained.

12. The system of claim 1, wherein detecting displacement further comprises determining a configuration between the plurality of physiological sensors, and comparing the determination with historical averages for the configuration between the plurality of physiological sensors.

13. A method of controlling oxygen supply for a subject, the subject having an airway, the method using a system that includes a pressure generator, a plurality of physiological sensors, and one or more position sensors, the method comprising:
   generating, by the pressure generator, a pressurized flow of breathable gas for delivery to the airway of the subject through a subject interface appliance;
   generating, by the plurality of physiological sensors, output signals conveying physiological information related to one or more physiological parameters of the subject;
   generating, by the one or more position sensors, output signals conveying position information related to one or more of the physiological sensors with respect to the subject, the subject interface appliance, and/or to other ones of the physiological sensors, wherein the one or more position sensors are not coupled to the subject and output video data;
   determining a level of arterial oxygen saturation of the subject based on the output signals generated by the physiological sensors;
   detecting displacement of the physiological sensors, subject interface appliance, and/or detect movement of the subject that could result in artifacts in determinations of the level of arterial oxygen supply, wherein the detections are based on the output signals generated by the one or more position sensors, wherein detecting displacement comprises detecting individual sensors of the plurality of physiological sensors in the video data, determining distances between the plurality of physiological sensors, and comparing those determinations with historical averages for distances between the plurality of physiological sensors; and
   adjusting one or more of the pressurized flow of breathable gas and/or a fraction of oxygen in the pressurized flow of breathable gas based on the determined level of arterial oxygen saturation and the detections of displacement.

14. The method of claim 13, further comprising:
   determining one or more positions of individual ones of the physiological sensors based on the generated output signals conveying position information.

15. The method of claim 14, further comprising:
   capturing image data such that the captured image data includes position information related to the subject,
   wherein detecting whether individual ones of the physiological sensors have been displaced is further based on the captured image data.

16. The method of claim 14, further comprising:
   generating output signals conveying information related to the delivery of the pressurized flow of breathable gas to the subject, and
   detecting whether delivery of the pressurized flow of breathable gas is obstructed based on the generated output signals conveying information related to the pressurized flow of breathable gas.

17. The method of claim 14, wherein determining whether individual ones of the physiological sensors have been displaced is accomplished by tracking locations of individual ones of the physiological sensors over time.

18. The method of claim 13, wherein the one or more position sensors include an image capture device configured to capture a top-view of the subject and insert, add, and/or superimpose a grid on a captured image to determine, relative to the grid, the position information related to one or more of the physiological sensors, and/or the subject interface appliance.

19. A system configured to control oxygen supply for a subject having an airway, the system comprising:
   means for generating a pressurized flow of breathable gas for delivery to the airway of the subject through a subject interface appliance;
   first means for generating output signals conveying physiological information related to one or more physiological parameters of the subject;
   second means for generating output signals conveying position information related to one or more of the first means with respect to the subject, the subject interface appliance, and/or the first means, wherein the second means for generating output signals conveying position information are not coupled to the subject and output video data;
   first means for determining a level of arterial oxygen saturation of the subject based on the output signals generated by the first means for generating;
   second means for detecting whether the first means for generating has been displaced in a way that could result in artifacts in determinations by the first means, wherein operation of the second means for detecting is based on the output signals generated by the second means for generating, wherein detecting displacement comprises detecting individual means of the first means for generating output signals conveying physiological information in individual frames of video data obtained from the second means for generating output signals conveying position information, determining the distances between the first means for generating output signals conveying physiological information, and comparing those determinations with historical averages for the distances between the first means for generating output signals conveying physiological information; and means for adjusting one or more of the pressurized flow of breathable gas and/or a fraction of oxygen in the pressurized flow of breathable gas based on determinations by the first means for determining and detections by the second means for detecting.

20. The system of claim 19, further comprising:
third means for determining one or more positions of the first means for generating based on the output signals generated by the first means for determining.

21. The system of claim 19, further comprising:
means for capturing image data such that the captured image data includes position information, wherein operation of the second means for detecting is further based on the captured image data.

22. The system of claim 19, further comprising:
third means for generating output signals conveying information related to the delivery of the pressurized flow of breathable gas to the subject,
wherein the second means for detecting further detects whether delivery of the pressurized flow of breathable gas is obstructed based on the output signals generated by the third means for generating.

23. The system of claim 19, wherein operation of the second means for detecting is accomplished by tracking one or more locations of the first means for generating over time.

24. The system of claim 19, wherein the second means for detecting is configured to capture a top-view of the subject and insert, add, and/or superimpose a grid on a captured image to determine, relative to the grid, the position information related to one or more of the physiological sensors, and/or the subject interface appliance.

* * * * *